(12) United States Patent
Hashimoto et al.

(10) Patent No.: US 11,839,603 B2
(45) Date of Patent: Dec. 12, 2023

(54) ASCORBIC ACID FORMULATION

(71) Applicant: FUJI OIL HOLDINGS INC., Izumisano (JP)

(72) Inventors: Arata Hashimoto, Izumisano (JP); Masaharu Kato, Izumisano (JP)

(73) Assignee: FUJI OIL HOLDINGS INC., Izumisano (JP)

( * ) Notice: Subject to any disclaimer, the term of this patent is extended or adjusted under 35 U.S.C. 154(b) by 391 days.

(21) Appl. No.: 16/975,906

(22) PCT Filed: Jan. 28, 2019

(86) PCT No.: PCT/JP2019/002648
§ 371 (c)(1),
(2) Date: Aug. 26, 2020

(87) PCT Pub. No.: WO2019/176330
PCT Pub. Date: Sep. 19, 2019

(65) Prior Publication Data
US 2021/0361617 A1     Nov. 25, 2021

(30) Foreign Application Priority Data
Mar. 16, 2018  (JP) ................ 2018-048776

(51) Int. Cl.
*A61K 31/375* (2006.01)
*A61K 9/107* (2006.01)

(52) U.S. Cl.
CPC .......... *A61K 31/375* (2013.01); *A61K 9/1075* (2013.01)

(58) Field of Classification Search
CPC .................................................. A61K 31/375
See application file for complete search history.

(56) References Cited

U.S. PATENT DOCUMENTS

| 7,109,237 B2 * | 9/2006 | Afriat | A61Q 17/00 |
| | | | 514/474 |
| 2007/0077220 A1 * | 4/2007 | Ramirez | A61P 3/02 |
| | | | 514/23 |
| 2013/0337024 A1 | 12/2013 | Serizawa | |
| 2020/0347300 A1 * | 11/2020 | Kato | C11B 5/0007 |

FOREIGN PATENT DOCUMENTS

| CN | 103379893 A | 10/2013 |
| EP | 2116223 B1 | 12/2015 |
| EP | 3425033 A1 | 1/2019 |
| JP | S62-77320 A | 4/1987 |
| JP | S64-3118 A | 1/1989 |
| JP | H09-235584 A | 9/1997 |
| JP | 2006008620 A | 1/2006 |
| WO | 2017/150558 A1 | 9/2017 |

OTHER PUBLICATIONS

WO 2017/150558A1 English Translation google patents (Year: 2022).*
Is the Environment in Your Mouth Alkaline or Acidic? New Image Dentistry Feb. 19, 2016 (Year: 2016).*
GCC CHM 151LL: Ascorbic Acid in Vitamin C Tablets (2009) (Year: 2009).*
International Search Report dated Mar. 26, 2019 for International Patent Application No. PCT/JP2019/002648, 2 pages with English translation.
Extended European Search Report dated Nov. 19, 2021 for corresponding European Application No. 19768057.2, 7 pages.
Beverage Technology, 2016, vol. 3, p. 66 (with English language translation).
Office Action dated Feb. 7, 2023 for corresponding Chinese Application No. 201980018460.8, 11 pages (with partial translation).

* cited by examiner

*Primary Examiner* — Brandon J Fetterolf
*Assistant Examiner* — Frank S. Hou
(74) *Attorney, Agent, or Firm* — MH2 TECHNOLOGY LAW GROUP, LLP

(57) ABSTRACT

An object of the present invention is to provide an ascorbic acid formulation that can be prepared by a simple method, and that has a reduced unpleasant taste and coloration. The inventors found that an ascorbic acid formulation that is in the form of a water-in-oil type emulsion, that comprises an aqueous phase with a pH of 4 or more and an average particle size of 300 nm or less, and that has a mass ratio of water/ascorbic acid of 0.05 to 0.40 has a reduced unpleasant taste and coloration; and accomplished the present invention. Additionally, the present invention can be prepared by a simple method.

4 Claims, No Drawings

ASCORBIC ACID FORMULATION

CROSS-REFERENCE TO RELATED APPLICATIONS

This application is a U.S. National Stage application of PCT/JP2019/002648, filed 28 Jan. 2019, which claims priority to Japanese Application No. 2018-048776, filed 16 Mar. 2018, the entire disclosures of which are incorporated herein by reference in their entireties.

TECHNICAL FIELD

The present invention relates to an ascorbic acid formulation.

BACKGROUND ART

Due in part to a proposal from Dr. Pauling of the United States, there is a demand for vitamin C formulations that are easily taken orally; i.e., ascorbic acid formulations. Ascorbic acid has a strong sour taste, and ascorbic acid salts have an unpleasant taste; thus, it is difficult to say that these can be easily taken orally as is.

Patent Literature 1 is an application relating to ascorbic acid formulations. Specifically, Patent Literature 1 discloses an L-ascorbic acid formulation containing oil and fat, and at least one of L-ascorbic acid, salts thereof, or esters thereof.

Patent Literature 2 discloses an L-ascorbic acid formulation in which L-ascorbic acid or a salt thereof is coated with a coating agent comprising 100 parts of oil and fat having a melting point of 50 to 80° C., and 1 to 10 parts by weight of a glycerin fatty acid ester selected from the group consisting of glycerin fatty acid monoesters or diesters.

PATENT LITERATURE

PTL 1: JP1987-77320A
PTL 2: JP1989-3118A

SUMMARY OF INVENTION

Technical Problem

An object of the present invention is to provide an ascorbic acid formulation that can be prepared by a simple method, and that has a reduced unpleasant taste and coloration.

Solution to Problem

The present inventors conducted extensive research to achieve the object. The specification of Patent Literature 1 discloses that a liquid obtained by suspending ascorbic acids in oil and fat is placed in a soft gelatin capsule, followed by drying; and the preparation thereof was complicated. Patent Literature 2 also requires subjecting ascorbic acid to a predetermined coating operation, and the preparation thereof was complicated.

The present inventors conducted further research, and found that an ascorbic acid formulation that is in the form of a water-in-oil type emulsion; that comprises an aqueous phase with a pH of 4 or more, and an average particle size of 300 nm or less; and that has a mass ratio of water/ascorbic acid of 0.05 to 0.40, has a reduced unpleasant taste and coloration. The present inventors thereby accomplished the present invention. In addition, the present invention can be prepared by a simple method.

Specifically, the present invention relates to the following.
(1) An ascorbic acid formulation satisfying all of the following requirements:
1: the ascorbic acid formulation being in the form of a water-in-oil type emulsion,
2: the ascorbic acid formulation comprising an aqueous phase having an average particle size of 300 nm or less,
3: the ascorbic acid formulation having a mass ratio of water/ascorbic acid of 0.05 to 0.40, and
4: the aqueous phase having a pH of 4 or more.
(2) A method for producing an ascorbic acid formulation comprising the following steps:
1: preparing an ascorbic acid-containing aqueous phase having a pH of 4 or more,
2: mixing an oil phase and the aqueous phase of step 1 to form a water-in-oil type emulsion, and
3: dehydrating the emulsion so that the water/ascorbic acid is 0.05 to 0.40, or the aqueous phase has an average particle size of 300 nm or less.
(3) The production method according to Item (2), wherein ascorbic acid and an ascorbic acid salt are used as ascorbic acid.
(4) The production method according to Item (3), wherein sodium ascorbate is used as the ascorbic acid salt.
(5) A method for reducing coloration of an ascorbic acid formulation, comprising the following steps:
1: preparing an ascorbic acid-containing aqueous phase having a pH of 4 or more,
2: mixing an oil phase and the aqueous phase of step 1 to form a water-in-oil type emulsion, and
3: dehydrating the emulsion so that the water/ascorbic acid is 0.05 to 0.40, or the aqueous phase has an average particle size of 300 nm or less.

Advantageous Effects of Invention

The present invention can provide an ascorbic acid formulation that can be prepared by a simple method, and that has a reduced unpleasant taste and coloration.

DESCRIPTION OF EMBODIMENTS

The ascorbic acid formulation according to the present invention is emulsified into a water-in-oil type; and the aqueous phase contains an ascorbic acid salt, or ascorbic acid and an ascorbic acid salt. Since the ascorbic acid formulation is emulsified into the water-in-oil type, it can be taken on a daily basis without difficulty; for example, as a dressing on vegetables. Additionally, the ascorbic acid formulation of the present invention is required to have no precipitation, because uneven distribution of ascorbic acid occurs.

In the present invention, the aqueous phase is, among raw materials, a water-soluble substance dissolved in water in the preparation stage; and the oil phase is, among raw materials, an oil-soluble substance dissolved in oil.

The preparation of the ascorbic acid formulation according to the present invention requires a dehydration step. When dehydration is performed, ascorbic acid or an ascorbic acid salt may be numerically present in the aqueous phase beyond its solubility, and the ascorbic acid or ascorbic acid salt may be precipitated. Specifically, in the prepared ascorbic acid formulation, a material derived from the aqueous phase in the production stage is sometimes simply referred to as the aqueous phase in the present invention, even when an ascorbic acid salt or the like are precipitated.

In the ascorbic acid formulation according to the present invention, the average particle size of the aqueous phase must be 300 nm or less. This value is more preferably 250 nm or less, even more preferably 200 nm or less. By setting the average particle size of the aqueous phase to an appropriate range, an ascorbic acid formulation having a reduced unpleasant taste and coloration can be obtained.

The average particle size measured herein may be either the particle size of an aqueous solution in which ascorbic acid and an ascorbic acid salt are dissolved, or the particle size obtained when ascorbic acid and an ascorbic acid salt are precipitated. As mentioned above, both are expressed as the average particle size of the aqueous phase.

The average particle size can be measured by using the Zetasizer Nano series (Malvern). A more specific measurement method is described in the Examples. The measured values of the average particle size may be inconsistent depending on the measuring method or the measuring device; however, in the present invention, a final judgment is made based on the value measured by the measuring method described in the Examples.

The present invention relates to an ascorbic acid formulation, and has a technical feature in that the particles of the aqueous phase containing ascorbic acid and/or an ascorbic acid salt are 300 nm or less.

The average particle size of the aqueous phase containing ascorbic acid and/or an ascorbic acid salt in the ascorbic acid formulation according to the present invention is 300 nm or less. Accordingly, a case in which a material having a large average particle size is, for instance, added to an oil phase to prepare an ascorbic acid formulation having an average particle size exceeding 300 nm as a whole of the aqueous phase and the material having a large particle size is also within the technical scope of the present invention.

In the ascorbic acid formulation according to the present invention, the mass ratio of water/ascorbic acid is 0.05 to 0.40. This value is more preferably 0.1 to 0.38, and even more preferably 0.15 to 0.35. When the value is in an appropriate range, an ascorbic acid formulation having a reduced unpleasant taste and coloration can be obtained.

For example, when an ascorbic acid salt is used, the amount of ascorbic acid used in the calculation of "water/ascorbic acid" herein is the value in terms of ascorbic acid contained in the ascorbic acid salt. Specifically, sodium ascorbate when used has a molecular weight of 198.11 g, while ascorbic acid has a molecular weight of 176.13 g; thus, if sodium ascorbate is used in an amount of A g, the amount in terms of ascorbic acid will be $A \times (176.13/198.11)$.

Similarly, calcium ascorbate when used has a molecular weight of 390.31 g, while ascorbic acid has a molecular weight of 176.13 g; thus, if calcium ascorbate is used in an amount of B g, the amount in terms of ascorbic acid will be $B \times ((176.13 \times 2)/390.31)$.

The amounts thus obtained are sometimes called ascorbic acid equivalents. Additionally, the value $(176.13/198.11) = 0.89$ is sometimes called an ascorbic acid coefficient in sodium ascorbate, and the value $((176.13 \times 2)/390.31) = 0.90$ is sometimes called an ascorbic acid coefficient in calcium ascorbate. Ascorbic acid, sodium ascorbate, and calcium ascorbate are sometimes simply referred to as VC, VC-Na, and VC-Ca, respectively; and the ascorbic acid coefficient is sometimes referred to as the VC coefficient. The VC coefficient in ascorbic acid is 1. Based on the above, "water/ascorbic acid" has the same meaning as "water/VC equivalent" and "water/ascorbic acid equivalent."

The pH of the aqueous phase of the ascorbic acid formulation according to the present invention must be 4 or more. The pH is more preferably 4.1 or more, and even more preferably 4.2 or more. The upper limit of the pH is more preferably 8.5 or less, and even more preferably 8 or less. By setting the pH in a suitable range, an ascorbic acid formulation having a reduced unpleasant taste and coloration can be obtained. If the pH is overly low, precipitation will occur in a relatively short time, and the resultant cannot be called an ascorbic acid formulation.

The pH can be adjusted by using various acids and alkalis, or by combining ascorbic acid and an ascorbic acid salt. The pH is preferably adjusted by combining ascorbic acid and an ascorbic acid salt. Combining ascorbic acid and sodium ascorbate is more preferable.

The ascorbic acid formulation according to the present invention is in the form of a water-in-oil type emulsion; however, various oils and fats can be used for the oil phase. Specifically, at least one oil and fat selected from soybean oil, rapeseed oil, rice oil, cottonseed oil, corn oil, palm oil, palm kernel oil, coconut oil, lard, beef tallow, fish oil, and algae oil; or at least one oil and fat that is subjected to at least one processing selected from separation, curing, and ester change can be used. At least one oil and fat selected from soybean oil, rapeseed oil, rice oil, cottonseed oil, and corn oil is more preferable.

An emulsifier can also be used, as necessary. Since the ascorbic acid formulation according to the present invention is in the form of a water-in-oil type emulsion, the emulsifier to be used is preferably an oil-soluble emulsifier. More specifically, an emulsifier having an HLB of 1 to 8, and more preferably 1 to 6, can be used. For example, a polyglycerol condensed ricinoleic acid ester is preferably used.

Next, the method for preparing an ascorbic acid formulation according to the present invention will be described with reference to examples.

In the present invention, an ascorbic acid salt, or ascorbic acid and an ascorbic acid salt is/are dissolved in water to prepare the aqueous phase; then, the pH is adjusted. When the ascorbic acid and ascorbic acid salt are used in an appropriate balance, the target pH can be obtained without separately adjusting the pH.

The ascorbic acid and ascorbic acid salt must be dissolved in the preparation of the aqueous phase. Whether they are dissolved can be determined, for example, by the fact that no precipitation occurs even after treatment with a centrifuge. More specifically, a state in which precipitation cannot be visually confirmed even when 5 ml of the aqueous phase is introduced into a ml-centrifuge tube at 20° C., and centrifuge is performed at 3000 G for one minute, is deemed to be a substantially dissolved state.

Since the ascorbic acid and ascorbic acid salt are dissolved in the aqueous phase in the production, an ascorbic acid formulation having a reduced unpleasant taste and coloration can be obtained. If the ascorbic acid and ascorbic acid salt are not dissolved in the aqueous phase at least in the stage of preparation, a particle size of 300 nm or less cannot be attained, even when the preparation of the ascorbic acid formulation is continued as is; and the effect of the present invention is not attained.

Next, the oil phase is prepared. The oil phase is obtained by optionally adding, to oil and fat, a raw material that is soluble in oil and fat; e.g., an emulsifier. If there are no raw materials that are soluble in oil and fat, only oil and fat form the oil phase.

After preparation of the oil phase, the aqueous phase is finely dispersed in the oil phase to form a water-in-oil type emulsion. Specifically, by gradually adding the aqueous phase while stirring the oil phase, a roughly emulsified liquid is formed. Furthermore, making the roughly emulsified liquid a finer emulsion by using a high-pressure homogenizer improves the stability thereof.

Next, the obtained water-in-oil type emulsion is dehydrated so that the mass ratio of water/ascorbic acid is 0.05 to 0.40. The dehydration can be performed by reducing pressure, or by introduction of a dry gas.

Although the mechanism of action is unclear, an ascorbic acid formulation that comprises the aqueous phase with an average particle size of 300 nm or less, and that has a reduced unpleasant taste and coloration, can be obtained by performing predetermined dehydration.

As described above, since the ascorbic acid formulation according to the present invention has a reduced unpleasant taste and coloration, has a large ascorbic acid content per weight, and is not in a capsule-like form, it can be added to various food to eat. This allows ascorbic acid to be taken in various situations Examples are described below.

EXAMPLES

Study 1

An emulsified liquid containing ascorbic acid was prepared according to the formulation shown in Table 1-1. The preparation was conducted in accordance with the "Preparation Method of Emulsified Liquid."

TABLE 1-1

| | | \multicolumn{6}{c}{Formulation} | | | | | |
|---|---|---|---|---|---|---|---|
| | | Study Example 1-1 | Study Example 1-2 | Study Example 1-3 | Study Example 1-4 | Study Example 1-5 | Study Example 1-6 |
| Aqueous phase | VC | 2 | 2 | 2 | 2 | — | 2 |
| | VC-Na | 1 | 2 | 4 | 6 | 7 | 8 |
| | Water | 8 | 8 | 8 | 8 | 8 | 8 |
| Oil phase | Emulsifier | 7 | 7 | 7 | 7 | 7 | 7 |
| | Oil and fat | 82 | 81 | 79 | 77 | 78 | 75 |
| Total | | 100 | 100 | 100 | 100 | 100 | 100 |
| pH | | | 3.6 | 4.0 | 4.3 | 5.4 | 7.5 | — |

The formulations are in mass %.

Ascorbic acid (VC) produced by Junsei Kagaku Co., Ltd., was used.
Sodium ascorbate (VC-Na) produced by DSM was used.
For the emulsifier, "CRS-75" polyglycerol condensed ricinoleic acid ester produced by Sakamoto Yakuhin Kogyo Co., Ltd. was used. HLB: 3.
For the oil and fat, Soybean shirashimeyu (refined soybean oil) produced by Fuji Oil Co., Ltd. was used.
The measurement values were filled in the pH column.
In Study Example 1-6, the aqueous phase was not in a dissolved state, and the preparation was cancelled.

Preparation Method of Emulsified Liquid

1. According to the formulation, ascorbic acid and/or an ascorbic acid salt were dissolved in water to prepare the aqueous phase. Preparation was continued only when the ascorbic acid and/or ascorbic acid salt were dissolved in the aqueous phase.
2. According to the formulation, the emulsifier was dissolved in the oil and fat to prepare the oil phase.
3. The aqueous phase and oil phase were stirred and mixed at 10000 rpm for 5 minutes with a homomixer (T.K. HOMO MIXER, Tokushu Kika Kogyo, Co., Ltd.).
4. Treatment was performed with a high-pressure homogenizer (Ecolyzer Labo-1, Sanmaru Machinery Co., Ltd.) while cooling with Mpa and 15 passes.

Study 2: Study of Dehydration of Fine Emulsified Liquid Obtained in Study 1

The fine emulsions obtained in Study Examples 1-1, 1-2, 1-3, and 1-4 were each dehydrated in a vacuum pump at a vacuum degree of 6 mmHg under heating (40° C.). Sampling was performed over time to measure the moisture content in each emulsion using a Karl Fischer moisture meter (Type 831 KF Coulometer Metrohm).

The moisture content in each stage and the "water/VC equivalent" in the aqueous phase were determined from the obtained data, and are shown in Table 2-1.

In addition, the color tone and the average particle size of samples in each stage were measured. The analysis was performed in accordance with the "Color Tone Analysis Method" and "Average Particle Size Measuring Method." The obtained results are shown in Table 2-1.

TABLE 2-1

| | | Study Example 1-1 | |
|---|---|---|---|
| | VC coefficient | Comparative Example 2-1 | Comparative Example 2-2 |
| VC | 1.00 | 2.0 | 2.0 |
| VCNa | 0.89 | 2.0 | 2.0 |
| Water | | 4.2 | 1.3 |
| VC equivalent | | 3.78 | 3.78 |
| Water/VC equivalent | | 1.11 | 0.34 |
| Average particle size (μm) | | 60 | 5530 |
| Color tone (value R) | | 1.1 | 2 |

TABLE 2-1-continued

Study Example 1-2

| | VC coefficient | Comparative Example 2-3 | Comparative Example 2-4 | Example 2-1 |
|---|---|---|---|---|
| VC | 1.00 | 2.0 | 2.0 | 2.0 |
| VCNa | 0.89 | 2.0 | 2.0 | 2.0 |
| Water | | 8.0 | 4.6 | 1.5 |
| VC equivalent | | 3.78 | 3.78 | 3.78 |
| Water/VC equivalent | | 2.12 | 1.21 | 0.40 |
| Average particle size (µm) | | 53 | 51 | 50 |
| Color tone (value R) | | 1.2 | 1.3 | 0.9 |

Study Example 1-3

| | VC coefficient | Comparative Example 2-5 | Comparative Example 2-6 | Comparative Example 2-7 | Comparative Example 2-8 | Example 2-2 | Example 2-3 |
|---|---|---|---|---|---|---|---|
| VC | 1.00 | 2 | 2 | 2 | 2 | 2 | 2 |
| VCNa | 0.89 | 4 | 4 | 4 | 4 | 4 | 4 |
| Water | | 8.0 | 5.6 | 3.9 | 2.7 | 1.9 | 1.5 |
| VC equivalent | | 5.56 | 5.56 | 5.56 | 5.56 | 5.56 | 5.56 |
| Water/VC equivalent | | 1.44 | 1.01 | 0.71 | 0.49 | 0.35 | 0.26 |
| Average particle size (µm) | | 56 | 53 | 54 | 56 | 54 | 51 |
| Color tone (value R) | | 2 | 1.5 | 1.6 | 1.8 | 1 | 1 |

Study Example 1-4

| | VC coefficient | Comparative Example 2-9 | Comparative Example 2-10 | Comparative Example 2-11 | Example 2-4 | Example 2-5 |
|---|---|---|---|---|---|---|
| VC | 1.00 | 2 | 2 | 2 | 2 | 2 |
| VC-Na | 0.89 | 6 | 6 | 6 | 6 | 6 |
| Water | | 8 | 5.2 | 4.2 | 2.2 | 1.7 |
| VC equivalent | | 7.33 | 7.33 | 7.33 | 7.33 | 7.33 |
| Water/VC equivalent | | 1.09 | 0.71 | 0.58 | 0.29 | 0.23 |
| Average particle size (µm) | | 56 | 56 | 55 | 53 | 54 |
| Color tone (value R) | | 2.1 | 2.2 | 2 | 1 | 1 |

Study Example 1-5

| | VC coefficient | Comparative Example 2-12 | Comparative Example 2-13 | Comparative Example 2-14 | Example 2-6 | Example 2-7 |
|---|---|---|---|---|---|---|
| VC-Na | 0.89 | 7 | 7 | 7 | 7 | 7 |
| Water | | 8 | 5.2 | 3.7 | 1.9 | 1.7 |
| VC equivalent | | 6.22 | 6.22 | 6.22 | 6.22 | 6.22 |
| Water/VC equivalent | | 1.29 | 0.84 | 0.60 | 0.31 | 0.27 |
| Average particle size (µm) | | 91 | 88 | 85 | 79 | 76 |
| Color tone (value R) | | 2 | 2.4 | 3.1 | 1 | 1 |

The compositions are in mass %.

The composition was calculated from the measured water value.

The samples of the Examples were evaluated by three panelists, but none of them experienced an unpleasant taste.

Color Tone Analysis Method 9 g of the ascorbic acid formulation that had been subjected to a deterioration acceleration test for one day under stirring at 40° C. and 200 rpm was added to a 1-inch cell.

The value R was measured with a Lovibond colorimeter.

Samples having a value R of 1.1 or less were deemed to have passed.

Average Particle Size Measuring Method 1.2 μL of an ascorbic acid formulation was diluted with 2 mL of hexane.

2. The particle size of water droplets in oil was measured with the Zetasizer Nano series (Malvern), and the calculated Z-average (nm) was defined as the average particle size.

Samples having an average particle size of 300 nm or less were deemed to have passed.

The setting values of the Zetasizer Nano series were as follows:

RI (Material) 1.444, Absorption (Material) 0, Temperature (Dispersant) 20 (° C.), Viscosity (Dispersant) 0.3 (cp), RI (Dispersant) 1.375, Equilibration time 60 (sec), Number of runs 10, Run duration 10, Number of measurements 1, Delay between measurements 0 (sec).

DISCUSSION

When the pH was remarkably lower than 3.6, precipitation occurred in the prepared sample at the beginning.

It was confirmed that in the samples having the predetermined pH, the color tone (R value) changed as the dehydration proceeded, and the color tone was deemed to have passed when the water/VC equivalent became 0.05 to 0.40. The average particle size when the color tone was deemed to have passed was 300 nm or less.

Study 3

An emulsified liquid containing ascorbic acid was prepared according to the formulation shown in Table 3-1. The preparation was conducted in accordance with the "Preparation Method of Emulsified Liquid."

TABLE 3-1

|  |  | Study Example 3-1 |
|---|---|---|
| Oil phase | VC-Ca | 3 |
|  | Water | 8 |
|  | Emulsifier | 7 |
|  | Oil and fat | 82 |
| Total |  | 100 |
| pH |  | 6.4 |

The formulations are in mass %.

Calcium ascorbate (VC-Ca) produced by Wako Pure Chemical Industries, Ltd., was used.

For the emulsifier, "CRS-75" polyglycerol condensed ricinoleic acid ester produced by Sakamoto Yakuhin Kogyo Co., Ltd. was used. HLB:3

For the oil and fat, soybean shirashimeyu (refined soybean oil) produced by Fuji Oil Co., Ltd. was used.

The measurement values were filled in the pH column.

Study 4: Study of Dehydration of Fine Emulsified Liquid Obtained in Study 3

The fine emulsions obtained in Study Example 3-1 were each dehydrated in a vacuum pump at a vacuum degree of 6 mmHg under heating (30 to 80° C.). Sampling was performed over time to measure the moisture content in each emulsion using a Karl Fischer moisture meter (Type 831 KF Coulometer Metrohm).

The moisture content in each stage and the "Water/VC equivalent" in the aqueous phase were determined from the obtained data, and are shown in Table 4-1.

In addition, the color tone and the average particle size of samples in each stage were measured. The analysis was performed in accordance with the "Color Tone Analysis Method" and "Average Particle Size Measuring Method." The obtained results are shown in Table 4-1.

TABLE 4-1

| | | Study Example 3-1 | | | | | |
|---|---|---|---|---|---|---|---|
| | VC coefficient | Comparative Example 4-1 | Comparative Example 4-2 | Comparative Example 4-3 | Comparative Example 4-4 | Example 4-1 | Example 4-2 |
| VC-Ca | 0.90 | 3 | 3 | 3 | 3 | 3 | 3 |
| Water | | 8 | 4.4 | 2.2 | 1.2 | 0.7 | 0.5 |
| VC equivalent | | 2.67 | 2.67 | 2.67 | 2.67 | 2.67 | 2.67 |
| Water/VC equivalent | | 3.00 | 1.65 | 0.82 | 0.45 | 0.26 | 0.19 |
| Average particle size (μm) | | 42 | 45 | 42 | 39 | 38 | 63 |
| Color tone (value R) | | 1.70 | 1.70 | 2.00 | 2.00 | 1.00 | 1.00 |

The compositions are in mass %.

The samples of the Examples were evaluated by three panelists, but none of them experienced an unpleasant taste.

DISCUSSION

It was confirmed that even when calcium ascorbate was used, the color tone changed as the dehydration proceeded, and the color tone was deemed to have passed when the water/VC equivalent became 0.05 to 0.40. The average particle size when the color tone was deemed to have passed was 300 nm or less.

The invention claimed is:

1. A food or food additive comprising an ascorbic acid formulation, wherein:
   (i) the ascorbic acid formulation is in the form of a water-in-oil type emulsion,
   (ii) the ascorbic acid formulation comprises an aqueous phase having an average particle size of 300 nm or less,
   (iii) the ascorbic acid formulation has a mass ratio of water/ascorbic acid of 0.05 to 0.40, and
   (iv) the aqueous phase has a pH of 4 or more,
   wherein the ascorbic acid formulation comprises ascorbic acid and an ascorbic acid salt.

2. A method for producing a food or food additive comprising an ascorbic acid formulation comprising the following steps:
   (1) preparing an ascorbic acid-containing aqueous phase having a pH of 4 or more,
   (2) mixing an oil phase and the aqueous phase of step (1) to form a water-in-oil type emulsion, and
   (3) dehydrating the emulsion so that the mass ratio of water/ascorbic acid is 0.05 to and the aqueous phase has an average particle size of 300 nm or less,
   wherein the ascorbic acid formulation comprises ascorbic acid and an ascorbic acid salt.

3. The method according to claim 2, wherein the ascorbic acid salt is sodium ascorbate.

4. A method for reducing coloration of a food or food additive comprising an ascorbic acid formulation, comprising the following steps:
   (1) preparing an ascorbic acid-containing aqueous phase having a pH of 4 or more,
   (2) mixing an oil phase and the aqueous phase of step (1) to form a water-in-oil type emulsion, and
   (3) dehydrating the emulsion so that the mass ratio of water/ascorbic acid is 0.05 to 0.40, and the aqueous phase has an average particle size of 300 nm or less,
   wherein the ascorbic acid formulation comprises ascorbic acid and an ascorbic acid salt.

* * * * *